United States Patent [19]

Hjertman et al.

[11] Patent Number: 5,679,111
[45] Date of Patent: Oct. 21, 1997

[54] DEVICE FOR DOSING A LIQUID PREPARATION

[75] Inventors: Birger Hjertman, Vällingby; Jan de Leeuw, Åkersberga, both of Sweden

[73] Assignee: Pharmacia & Upjohn Aktiebolag, Stockholm, Sweden

[21] Appl. No.: 362,433

[22] PCT Filed: Apr. 22, 1994

[86] PCT No.: PCT/SE94/00358

§ 371 Date: Mar. 10, 1995

§ 102(e) Date: Mar. 10, 1995

[87] PCT Pub. No.: WO94/25090

PCT Pub. Date: Nov. 10, 1994

[30] Foreign Application Priority Data

Apr. 30, 1993 [SE] Sweden .................. 9301494

[51] Int. Cl.$^6$ .................................................. A61M 5/00
[52] U.S. Cl. ................. 604/135; 604/207; 604/208
[58] Field of Search ........................ 604/135, 207, 604/208

[56] References Cited

U.S. PATENT DOCUMENTS

| | | | |
|---|---|---|---|
| 2,413,303 | 1/1946 | Folkman | 604/135 |
| 4,865,591 | 9/1989 | Sams | 604/208 |
| 5,279,585 | 1/1994 | Balkwill | 604/207 |
| 5,304,152 | 4/1994 | Sams | 604/208 |

FOREIGN PATENT DOCUMENTS

| | | |
|---|---|---|
| B-22763/83 | of 1983 | Australia . |
| 2276383 | 1/1983 | Australia . |

Primary Examiner—Sam Rimell
Assistant Examiner—Luke Yeh
Attorney, Agent, or Firm—Pollock, Vande Sande & Priddy

[57] ABSTRACT

An injection device is provided for a continuously variable metering and administering of a liquid preparation and having a holder device for a multi-dose injection cartridge, the rear piston of which may be moved forward by means of a piston rod. The piston rod is provided with releasable locking means having at least one longitudinal groove having a wedge-shaped cross section and at least one locking lug having a cross section adapted to that of the groove, and means for urging the locking lug into said grooves to lock the movement of the piston rod, or to release the locking lug from said groove to free the movement of said piston rod. At its rear end, the piston rod is connected to a spring device for moving the piston rod forward and to a device for determining the stroke of the piston rod when the preparation is administered.

8 Claims, 4 Drawing Sheets

DEVICE FOR DOSING A LIQUID PREPARATION

DESCRIPTION

1. Technical Field

The present invention is directed to a device for dosing and administering a liquid preparation. More specifically, the invention refers to repeated dosing and administering of liquid pharmaceutic preparations by parenteral injection from a multi-dose container. Still more specifically, the invention refers to a device for infinitely variable dosing and administering of liquid pharmaceutic preparation by parenteral injection from a multi-dose container, such as an injection cartridge.

2. Background Art

International patent application PCT/SE92/00654 describes a method for repeated dosing of a liquid preparation of a pharmaceutically active agent by administration from a multi-dose container having a defined volume. What characterizes this method is that the amount of the preparation to be dosed is selected to be 1/N of the volume of the multi-dose container, N being an integer having a value of 2 or higher. The value of N is selected and set before the repeated dosing of the preparation from the multi-dose container is started, and is maintained unchanged through a series of N successive administrations from the multi-dose container, which has consequently then been emptied. As a second variable or degree of freedom is used the concentration of the liquid preparation, such that the portion 1/N will give the desired dose of the pharmaceutically active agent. By using a series of containers with preparations of different concentrations, and a plurality of values for N, it is clear that a great number of different doses of the active agent can be obtained.

Through the method and system described, it has thus become possible to administer a number of doses of a liquid preparation from a multi-dose container in such a way that essentially no residue of the preparation is obtained. This is of considerable importance when very expensive pharmaceutical agents are to be administered, such as growth hormones.

The above-mentioned international application PCT/SE92/00654 also discloses a device for the repeated dosing of a liquid preparation from a multi-dose container. Such a device comprises a holder device for a multi-dose container having a defined volume and containing a preparation having a defined composition, and the multi-dose container is provided with a fixed front wall, through which may be arranged an outlet for the preparation, and a movable rear wall, which may act as a piston for expelling the preparation through said outlet, and a piston rod, by which the rear movable wall may be urged forwards. What characterizes the device is that the piston rod is provided with releasable blocking means by which the forward movement of it is limited to a predetermined length, which corresponds to a forward movement of the rear movable wall corresponding to 1/N of the multi-dose container, N being an integer having a value of 2 or higher.

It is to be noted that in the following specification and claims, the expressions "front" and "forward" refer to the direction in which the liquid preparation is made to flow when it is administered. Conversely, the opposite direction is denoted as "rear" and "rearward", respectively.

In a preferred embodiment of the device described above, it comprises a barrel for holding at its front end part an injection cartridge and a piston rod for actuating said injection cartridge to expel a set amount of the liquid preparation from the cartridge. The releasable blocking means comprise a fixed chuck and a movable chuck which clamp around the piston rod through the action of a spring force, said clamping action being releasable by reducing said spring force. Thus, the front chuck is fixed in relation to the barrel and the cartridge, and its clamping action around the piston rod may be actuated to lock it securely to the chuck, or may be released to allow the piston rod to move in relation to the chuck. The rear chuck is movable in relation to the barrel and the cartridge, and can be moved along the piston rod, when its clamping action is released, or may follow the piston rod in its movement, when the clamping action is actuated.

When a measured dose of the liquid preparation is to be administered, the rear chuck is moved rearwards against a spring force by means of a yoke arrangement, which at the same time releases the clamping action of the chuck such that it can move along the piston rod at the same time as said piston rod is locked in place by means of the clamping action of the front chuck. The rearward movement of the rear chuck is limited by stopping means, and the clamping action of this chuck is actuated again in this rear position, so that the chuck is locked in place in said rear position. The distance that the rear chuck is moved rearward is predetermined and set in the device, and determines the magnitude of the dose of the liquid preparation.

When a dose is to be administered, the clamping action of the front chuck is released. The spring force will now urge the rear chuck and the piston rod forward the same distance as that set for the rearward movement. Under the influence of the spring force, the piston rod will act on the rear movable wall of the injection cartridge to urge said wall forward to expel a metered dose of the liquid preparation from the cartridge.

These two readying and administering steps may then be repeated as many times as desired, until the cartridge has been emptied.

The important feature of the device described above is that the dose set can be infinitely varied. This is necessary for administring in accordance with the method described, where no residue should be left after administering a determined number of doses. This method and device should not be confused with the prior art methods and devices for administering liquid preparations. The prior art devices for repeated administration from a multi-dose cartridge usually consist of an injection device which comprises a mechanism for a stepwise forward movement of the rear movable wall of the injection cartridge, such as a screw or ratchet mechanism. The steps which are possible with this type of mechanism are fixed and a dose can only be determined by a given number of steps. Thus, the prior art mechanism may be adapted to the injection cartridge in such a manner that an advancement of the mechanism by one step will give a dosed amount of, for example, ⅛ of the volume of the cartridge. However, the mechanism cannot the be easily adapted to give a dose of, for example, ⅐, ⅑ or ⅒ of the volume of the cartridge. This means that only a limited number of dose amounts are possible without giving a residue.

In contrast to this, it will always be possible with the device described above to set a dose which is 1/N of the volume of the cartridge, N being an integer. The value of N may be set on the device before a series of administrations is started, and it cannot then be easily changed. By providing a suitable range of cartridges with varying concentrations of the preparation and a suitable range of values for N, it is possible to obtain a wide range of possible doses. This range of doses may then be presented in a table, from a computer memory, or in a nomograph, for easy reference by the physician.

The device described in the international patent application PCT/SE92/00654 has turned out to work well in the practice of the method described. However, there is room for some improvements. Thus, the arrangement of two separate chucks for alternately locking and releasing the piston rod is rather complicated. A considerable spring force is necessary to grip and lock the piston rod securely, and this also makes it necessary to use a considerable force when the chucks are to be released, such as when an injection is to be administered. This may make the administering difficult in those cases when the patient is to administer the injections to himself, such as in the ambulatory treatment of diabetes with insulin. After repeated use with a number of injection cartridges, this may also lead to wear on the piston rod, such that the accuracy of the metering of the dose will be decreased.

These disadvantages are eliminated by the injection device of the present invention.

SUMMARY OF THE INVENTION

According to the present invention, an injection device is provided for an infinitely or continuously variable metering and administering of a liquid preparation, and comprising a holder device for a multi-dose injection cartridge which comprises a fixed front wall through which may be arranged a liquid connection for discharging the preparation, and a rear, movable wall which may be moved forward by means of a piston rod to expel the preparation from the cartridge. What characterizes the invention is that the piston rod is provided with releasable locking means, having at least one longitudinal groove having a wedge-shaped cross-section, and at least one locking lug having a cross-section adapted to that of the groove, and means for urging the locking lug or lugs into the groove or grooves to lock the longitudinal movement of the piston rod, and to release the urging to free the piston rod, and that the piston rod at its rear end is connected to a spring device for moving the piston rod forward at the administering, and a device for setting the stroke of the piston rod when the preparation is administered.

In a preferred embodiment, the piston rod is provided with at least two longitudinal grooves which are evenly spaced around the circumference of said piston rod, and a corresponding number of locking lugs. Around their outer circumference, the lugs have a conical shape and are surrounded by a tubular sleeve, which rests against the outer conical parts of the locking lugs and can be moved in the longitudinal direction, such that by this movement it can exert a pressure against the locking lugs and urge them into the grooves to lock the piston rod, or release the pressure on the locking lugs to free the piston rod.

In a still further preferred embodiment, the tubular sleeve is pressed against the locking lugs by means of a spring pressure in the longitudinal direction, to urge the locking lugs into the grooves. By means of a lever device, the tubular sleeve may be displaced in the longitudinal direction against the spring pressure to release the pressure on the locking lugs, to free the piston rod.

BEST AND VARIOUS MODES FOR CARRYING OUT INVENTION

Figure 1:
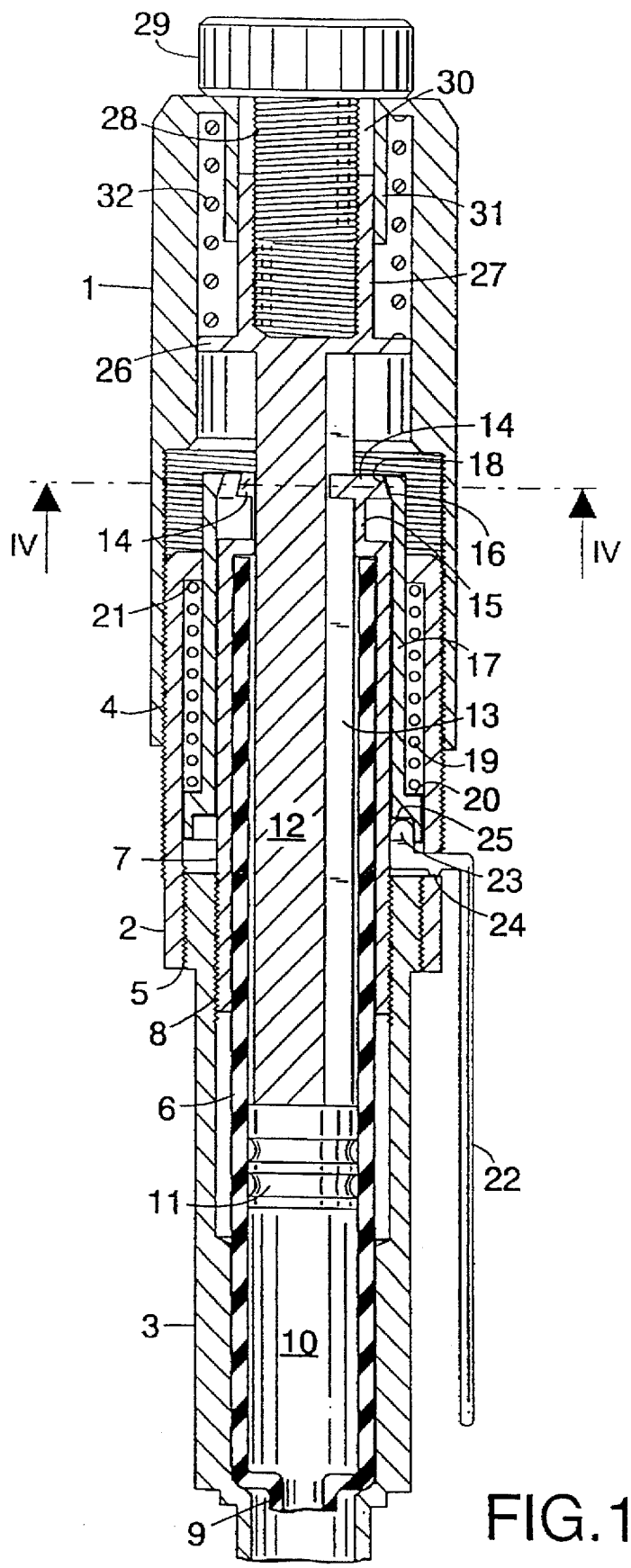
FIG. 1 shows an injection device according to the invention before it has been readied for an injection.

FIG. 1 of the drawings shows a sectional view of an injection device according to the invention. The device comprises a holder, which comprises a rear sleeve 1 and a front sleeve, which in the embodiment shown consists of two joined sleeves 2 and 3. These three sleeves are joined together by means of threads 4 and 5, respectively, to hold an injection cartridge 6, which in its turn is secured by an interior sleeve 7, which is joined to the front sleeve 3 by means of the thread 8.

The injection cartridge 6 is of a conventional design and has a bottleneck-shaped front end 9. This front end 9 is provided with a conventional end closure or wall, which usually comprises a rubber septum which is held in place by a metal capsule which has an opening in its center part, where the septum is exposed. Through this opening, a needle may be inserted through the septum to provide a liquid connection with the interior of the cartridge and an outlet for the liquid preparation inside the cartridge. As the arrangements at the front end of the cartridge are of a completely conventional nature, they are not shown in detail.

The chamber 10 of the cartridge 6 contains a liquid preparation and is closed at its rear end by a movable wall or piston 11, which is actuated by a piston rod 12.

The piston rod 12 is provided with three longitudinal grooves 13, which have a wedge-shaped cross-section. This can be seen more clearly in FIG. 4, which is a cross-sectional view along IV—IV in FIG. 1. These grooves extend along the whole length of the piston rod, except for its rear end part.

In the longitudinal grooves 13 are arranged three locking lugs 14, which also have a wedge-shaped cross-section adapted to that of the grooves 13. This can be seen more clearly in FIGS. 4 and 5. The lugs 14 are mounted on upright stalks 15 which extend from the rear end of the interior sleeve 7. These stalks should have a certain springiness, but will not have to take up any great bending angles. The spring action of the stalks 15 will strive to pull the locking lugs 14 out of the grooves 13, but this spring force does not have to be very great.

Figure 4:
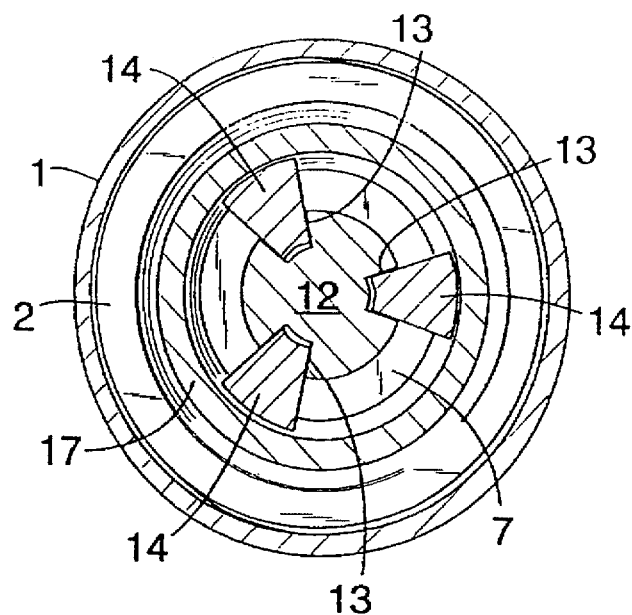
FIG. 4 shows a sectional view along the line IV—IV in FIG. 1.
Figure 5:
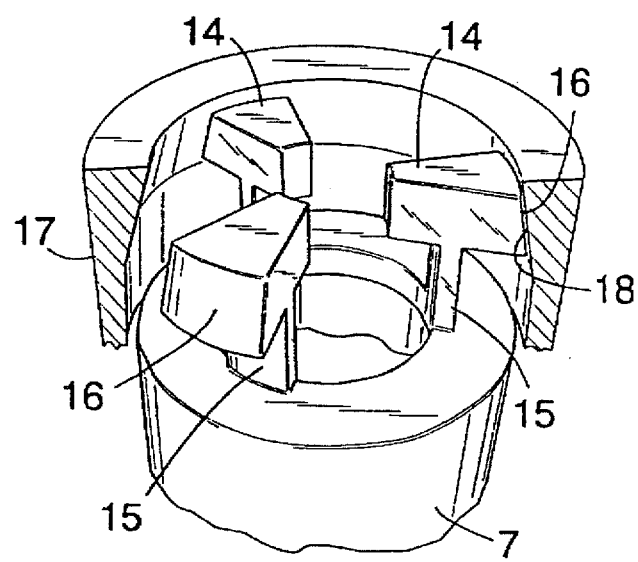
FIG. 5 shows a view in perspective of the locking arrangement for the piston rod. In all the figures, like parts have the same reference numbers.

The outer edges 16 of the locking lugs 14 form parts of a circle, and their circumferential surfaces are conical with their smaller diameter at the rear, as can be seen in FIGS. 4 and 5. The locking lugs 14 are surrounded by a tubular actuating sleeve 17, which is arranged outside of the interior sleeve 7 and coaxially therewith. The rear part of the actuating sleeve 17 has an interior surface 18, which is conical and is adapted to the conical surface 16 of the circumference of the locking lugs 14, such that the interior surface 18 abuts against the exterior conical surface 16 of the locking lugs 14. Furthermore, a spring 19 is arranged in a space between the actuating sleeve 17 and the front sleeve 2. This spring 19 rests against a shoulder 20 on the actuating sleeve 17 and a shoulder 21 on the front sleeve 2 and exerts a pressure on these two shoulders, such that it strives to urge the actuationg sleeve 17 forward. By this action, the interior conical surface 18 of the actuating sleeve 17 will press against the exterior conical surface 16 of the locking lugs 14, such that these lugs are urged into the grooves 13, to securely lock the piston rod and prevent any longitudinal movement thereof.

This is an important feature of the present invention. By their wedge action, the locking lugs 14 will exert considerable pressure against the walls of the grooves 13 when they are in their locking positions, without the force of the spring 19 acting on the locking lugs 14 through the intermediary of the conical surfaces 16 and 18 having to be excessively great.

The locking action by the lugs 14 on the piston rod 12 may be released by moving the actuating sleeve 17 rearward. For this, a lever device 22 is arranged through an opening in the front sleeve 2. The lever has an external arm 22 and an internal arm 23 and rests on a projection 24, which provides a fulcrum. The end of the internal arm 23 rests against a forward-facing shoulder 25 of the actuating sleeve 17, and through the action of the spring 19, a contact between the shoulder 25 and the internal arm 23 of the lever is assured at all times. Thus, when the external arm 22 of the lever is moved inwards toward the front sleeve 3, the internal arm 23 will turn about the fulcrum 24 and be displaced rearwards, such that the actuating sleeve 17 is moved rearwards. The inward-facing surface 18 of the actuating sleeve at its rear end will then no longer press against the outward-facing surfaces 16 of the locking lugs 14, which will then no longer be urged against the walls of the grooves 13 in the piston rod 12. The piston rod will then be free to move in relation to the front sleeves 2 and 3 and the injection cartridge 6.

At its rear end, the piston rod 12 is provided with a transversal flange 26 and a coaxial threaded tubular sleeve 27. A screw 28 can be screwed into the threaded sleeve 27 for a given distance, which determines the amount of the preparation to be administered in a dose, as will be explained in more detail in the following. The screw 28 is provided with a stopping device 29, which may be shaped as a knurled wheel for easy setting of the dose. However, other shapes are also possible.

In the drawing, the threaded sleeve 27 is shown having an internal thread and the screw 28 as having an external thread. However, it will be understood that threaded sleeve 27 may instead have an external thread, in which case the screw 28 will be a sleeve having an internal thread. This will not affect the function of the device.

The rear sleeve 1 is provided at its rear end with a central opening 30, through which the screw 28 can pass, but not the stopping device 29. This opening 30 is connected to an internal rear sleeve 31, which extends forward from the rear opening 30 for a determined distance inside the rear sleeve 1. The threaded tubular sleeve 27 at the rear end of the piston rod 12 fits inside the internal rear sleeve 31 and may be rotated or displaced longitudinally therein. Between the outer wall of the internal rear sleeve 31 and the internal wall of the rear sleeve 1 is provided a tubular space, and in this space is arranged a helical spring 32 between the rear face of the flange 26 and the internal rear end wall of the rear sleeve 1. The force of this spring 32 strives to push the flange 26 and the piston rod 12 forward and provides the force necessary for expelling the liquid preparation from the chamber 10 of the injection cartridge 6 when an injection is to be administered. The forward movement of the piston rod, however, is restricted by the stopping device 29, which rests against the rear end of the rear sleeve 1, and the possible movement of the piston rod 12 forward is determined by how far the screw 28 has been screwed into the threaded sleeve 27.

The rear sleeve 1 may be screwed onto the front sleeve 2 by means of the thread 4. When this is done, the piston rod 12 will be moved rearward in relation to the rear sleeve 1, and the flange at its rear end will approach the forward edge of the internal rear sleeve 31, and when it abuts this edge, no further movement rearward is possible. As is apparent from the foregoing, the distance that the piston rod 12 can be moved rearward is determined by how far the screw 28 has been screwed into the threaded sleeve 27. It is also realized that during this movement rearward by the piston rod 12, it is locked in place relative to the injection cartridge 6 and the front sleeves 2 and 3 by the locking lugs 14, which are being urged into the grooves 13 in the piston rod by the pressure of the actuating sleeve 17.

Figure 2:
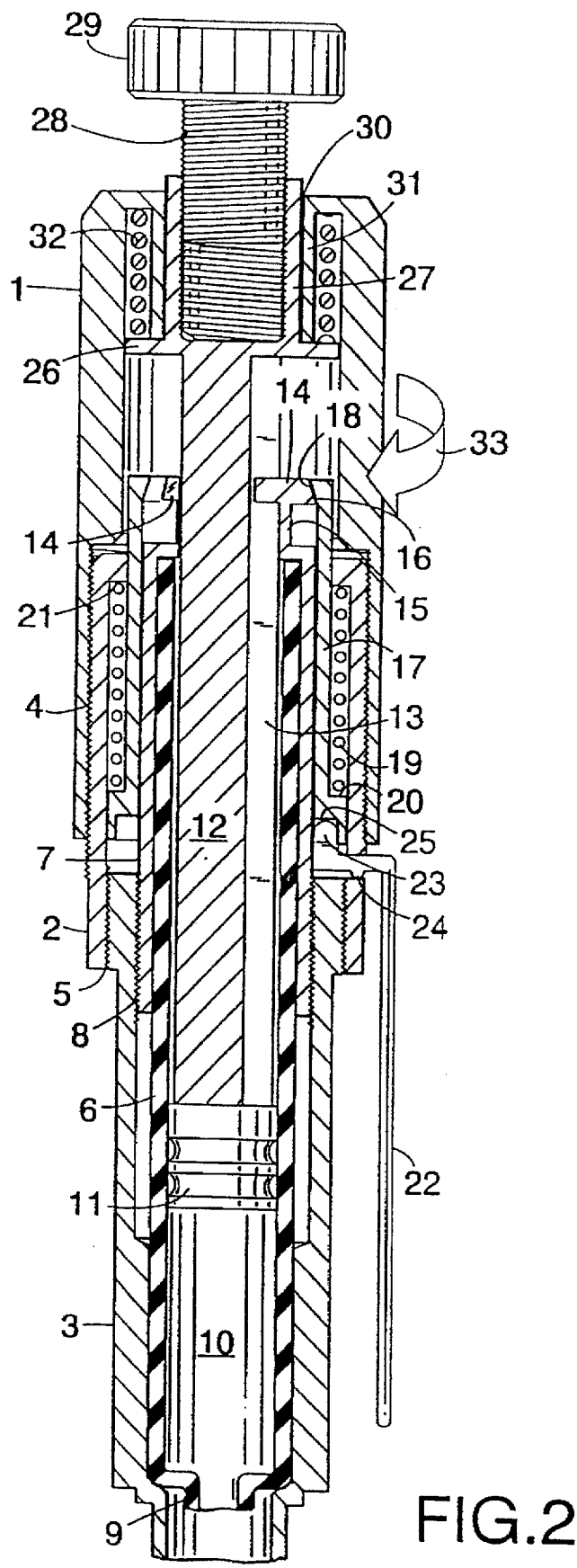
FIG. 2 shows the device after it has been readied for an injection.

FIG. 2 shows the device of the invention after the rear sleeve 1 has been screwed onto the front sleeve 2 in the direction of the arrow 33 until the flange 26 at the rear end of the piston rod 12 abuts the forward edge of the internal rear sleeve 31. The spring 32 has been compressed between the rear face of the flange 26 and the front face of the rear end wall of the rear sleeve 1. Through the relative movement of the piston rod 12, the threaded sleeve 27 at its rear end and the screw 28 with its stopping means 29 now protrude from the rear end of the rear sleeve 1.

The piston rod 12 is still gripped by the locking lugs 14, which are urged into the grooves 13 by the pressure from the inclined surface 18 of the actuating sleeve 17. This sleeve is urged forward by the spring 19.

Figure 3:
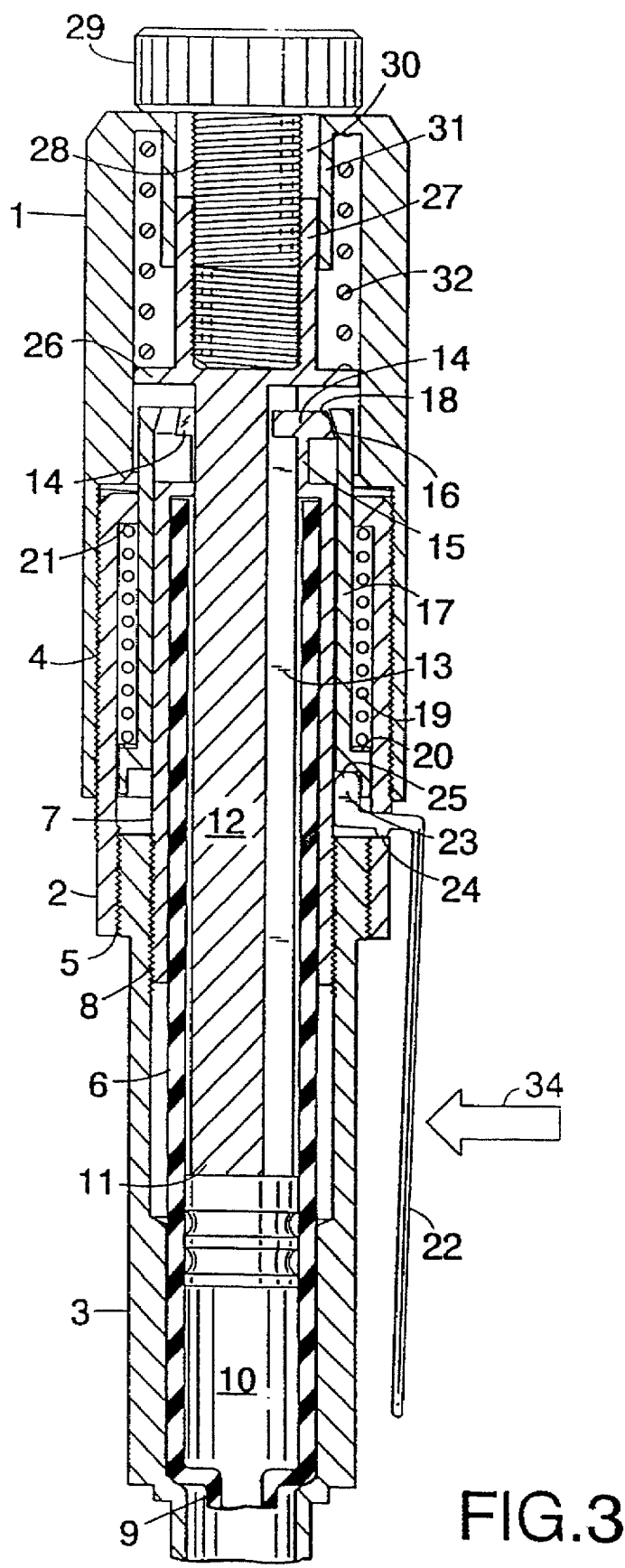
FIG. 3 shows the device after an injection has been administered.

FIG. 3 shows the injection device of the invention after an injection has been administered. The external arm 22 of the lever device has been moved inward, as is shown by the arrow 34, to rotate lever about the fulcrum 24 such that the end of the internal arm 23 has been moved rearward. The internal arm 23 has acted on the shoulder 25 of the actuating sleeve 17 to displace it rearwards against the pressure of the spring 19. This rearward movement of the actuating sleeve 17 will also move the interior conical surface 18 at its rear end away from the corresponding conical surfaces 16 of the locking lugs 14. These lugs will then no more be forced into the grooves 13 to lock the piston rod 12, which is now free to move forward under the influence of the compressed spring 32. As the forward end of the piston rod rests against the rear face of the rear movable wall or piston 11, the pressure of the spring 32 will thus displace the piston 11 forward for a given distance, to expel a determined amount of the liquid preparation from the chamber 10 of the injection cartridge 6.

The forward travel of the piston rod 12 is stopped when the stopping means 29 at the rear end of the screw 28 abuts the rear end of the rear sleeve 1. It will thus be seen that the amount of the liquid preparation administered from the injection cartridge 12 is determined by the distance that the piston rod 12 is moved forwards, and this distance in turn is determined by the distance that the screw 28 has been screwed into the threaded sleeve 27. It is preferred that the setting of the dose of the injectable preparation is arranged in such a way that the setting cannot be easily changed. Thus, the arrangement of the screw 28 with its stopping means 29 and the threaded sleeve 27 may be provided with some locking means, so that the dose set by the physician, the pharmacist or by the patient himself cannot be easily changed involuntarily. Such means are within the competence of a person skilled in this art.

When the pressure on the external arm 22 of the lever is released, the spring 19 will again act on the shoulder 20 of the actuating sleeve 17 to move it forward. The conical surface 18 at its rear end will again get into contact with the conical surfaces 15 of the locking lugs 14, to urge them into the grooves 13 in the piston rod 12. The piston rod 12 will now be locked in relation to the injection cartridge 6, and the complete device will again be in the state shown in FIG. 1.

FIG. 4 shows a sectional view along the line IV—IV in FIG. 1. It is here seen how the locking lugs 14 are urged into the grooves 13 of the piston rod 12, by the action of the rear end of the actuating sleeve 17. The piston rod 12 will now be locked by the wedge action of the locking lugs 14 being forced into the grooves 13.

FIG. 5 shows a view in perspective of the arrangement of the locking lugs. For clarity, the piston rod 12 is not shown. It is seen how the locking lugs 14 are mounted on stalls 15 at the rear end of the interior sleeve 7 which secures the injection cartridge (not shown). The outer peripheral parts 16 of the locking lugs 14 have a conical shape and are surrounded by the actuating sleeve 17. At the rear end of this sleeve, its internal wall 18 has a conical shape which is adapted to the shape of the peripheral parts 16 of the locking lugs 14. Thus it will be seen that if the actuating sleeve 17 is moved forward, its internal conical part 18 at its rear end will abut against the external peripheral parts 16 of the locking lugs 14. This axial movement will then be translated into a radial movement inward of the locking lugs 14.

In the embodiment shown in the drawings, the device of the invention is intended to be disposable, i.e. there are no provisions for an easy removal of a finished injection cartridge and the insertion of a fresh one. The device is intended to be charged with an injection cartridge when it is assembled, and to be discarded after the cartridge has been emptied. However, it is clear to those skilled in the art that the device of the invention may also be designed as a re-usable device, and the modifications necessary for this are apparent to such skilled persons. For example, one such modification may be to arrange the front sleeve 3 in two coaxial tubular parts, which may be screwed into each other or otherwise assembled. In this way, a finished cartridge may be pulled out forwards, when the front end has been removed, and a fresh cartridge be inserted. The two parts of the front sleeve 3 are then assembled again, and the device may be readied for use.

The function of the device of the invention will now be described in detail:

When the device is to be readied for an injection, it is in the state shown in FIG. 1 of the drawings. An injection cartridge 6 has been inserted into the front sleeve 3 and is secured by the interior sleeve 8. The front end of the piston rod 12 rests against the rear face of the piston 11, and the piston rod is secured in place by the locking lugs 14, which are forced into the grooves 13 to lock any axial movement of the piston rod. The spring 19 urges the actuating sleeve 17 forward, and the inclined surface at the rear end of this sleeve forces the locking lugs 14 into the grooves 13.

At the rear end of the piston rod 12, the flange 26 is situated at a distance from the front end of the rear interior sleeve 31. This distance is determined by how far the screw 28 has been screwed into the threaded tubular sleeve 27. The stopping device 29 rests against the rear end of the rear sleeve 1.

To prepare the device for an injection, the user turns the rear sleeve in the direction shown by the arrow 33 in FIG. 2. The rear sleeve 1 will then be screwed onto the front sleeve 2 by means of the thread 4, and the piston rod 12 with its flange 26 and the threaded tubular sleeve 27 with the screw 28 and the stopping device 29 will move rearwards in relation to the rear sleeve 1. After the rear sleeve 1 has been screwed onto the front sleeve 2 for a predetermined distance, the flange 26 on the piston rod 12 will abut the front end of the rear interior sleeve 31, and no further movement is possible. The screw 28 and the stopping device 29 will now protrude from the opening 30 in the rear end face of the rear sleeve 1, and the spring 32 has been compressed.

During this preparation process, the piston rod 12 has been locked in place by the locking lugs 14, which have been forced into the grooves 13 by the action of the spring 19 and the inclined surfaces 16 and 18. Thus, there has been no movement of the piston rod 12 in relation to the injection cartridge 6.

When the injection is to be administered, the external arm 22 of the lever is moved inwards, as is shown by the arrow 34 in FIG. 3. The lever will then turn about the fulcrum 24 such that the end of the internal arm 23 will move rearward to act on the shoulder 25 of the actuating sleeve 17. This sleeve will then be moved rearwards against the pressure of the spring 19, and the conically inclined surface 18 at its rear end will no longer press against the correspondingly inclined surfaces 16 of the locking lugs 14. The locking lugs 14 will then no longer be urged into the grooves 13, and through the spring action of the stalks 15, the locking lugs 14 will withdraw slightly from said grooves 13. The piston rod 12 will then be free to move forward under the influence of the rear spring 32 and will move the piston 11 forward to expel a predetermined amount of the injectable preparation from the chamber 10 of the injection cartridge 6. The forward travel of the piston rod 12 is ended when the stopping device 29 abuts the rear end of the rear sleeve 1, and the distance travelled is determined, as shown in the foregoing, by the distance that the screw 28 has been screwed into the threaded tubular sleeve 27.

The piston rod 12 will be free as long as the pressure inward on the external arm 22 of the lever is maintained. When this pressure is released, the actuating sleeve 17 will again move forward by the influence of the spring 19, and the inclined surface 18 at the rear end of this sleeve will again exert pressure on the circumferential surfaces 15 of the locking lugs 14, forcing them into the grooves 13 to lock the piston rod 12 in place.

It will be seen that the internal arm 23 of the lever and the actuating sleeve 17 will not have to be displaced for any great distance to effect the locking or unlocking, respectively, of the movement of the piston rod 12. This is a consequence of the wedge effect being utilized, and is an important advantage of the invention.

The device is now again in the state shown in FIG. 1, and the process described above may be repeated until the injection cartridge is empty.

It is to be noted that the injection is administered by means of the force exerted by the rear spring 32, which means that the device has auto-injecting properties. Thus, the user only has to insert the needle at the site of injection and push the lever 22 inward, but will not have to maneuver the piston rod itself to carry out the injection. This greatly simplifies the process of administering the injections, and is an added advantage of the device of the invention.

In the embodiment of the invention shown in the drawings, the injection cartridge has been shown as a single-chamber cartridge. However, it is clear to those skilled in the art that also dual-chamber cartridges can be used in the device. Such dual-chamber cartridges comprise two chambers separated by a movable wall or piston. The front chamber usually contains a solid component of the injectable preparation, and the rear chamber contains a liquid component to dissolve the solid component. When the rear piston of the dual-chamber cartridge is moved forward, the pressure will be transmitted through the largely incompressible liquid to move the separating wall forward until a bypass connection between the two chambers is opened. The liquid component will then flow over into the front chamber to dissolve the solid component, and the solution formed may then be administered as described in the foregoing. Dual-chamber cartridges are well-known and are used for injectable preparations which are unstable in the form of a solution and therefore will have to be prepared immediately before the administration.

The modifications necessary for adapting the device of the invention to the use of a dual-chamber injection cartridge can easily be determined by those skilled in the art. When a dual-chamber cartridge is used in a device of the invention, the user will first make a suitable number of "dry run" administrations to advance the rear piston of the cartridge sufficiently far to urge the liquid component over into the front chamber of the cartridge. The device is then ready to be used as described in the foregoing. Other processes for mixing the two components prior to injection are also apparent to those skilled in the art.

The design in detail of the device of the invention is within the competence of a person skilled in the art, once the inventive idea has been understood. Also ths selection of suitable materials for the various parts of the device is no problem for those skilled in the art. Conventionally, such materials as stainless steel, various plastic and rubber materials, and glass are used for the parts of the device. It goes without saying that all materials must be able to withstand heat sterilization.

It is to be noted that the expression "liquid injectable preparation" is intended to encompass not only solutions, but also emulsions, suspensions and other dispersions which are pharmaceutically acceptable for parenteral injection.

Through the present invention, it has been possible to provide a device for injection where the dose to be injected may be set in an infinitely variable manner, such that the device may be used for administering injections in accordance with the system described in the foregoing, where no residues are obtained. This is an important advantage, especially when very expensive preparations are to be administered.

It is to be noted that the embodiments described in the foregoing specification and drawings are only examples, and are not intended to restrict the scope of the invention in any way. A number of modifications and variations are possible and apparent to those skilled in the art, and the invention is only restricted by the scope of the appended claims.

We claim:

1. An injection device for continuously variable metering and administering of a liquid injectable preparation, comprising a holder device for a multi-dose injection cartridge which comprises a front fixed wall through which may be arranged a liquid connection for discharging the preparation, and a rear movable wall which may be moved forward by means of a piston rod to expel the preparation from said cartridge, characterized in that the piston rod is provided with releasable locking means consisting of at least one longitudinal groove having a wedge-shaped cross-section and at least one locking lug having a cross-section adapted to that of the groove, and means for urging said locking lug into said groove to lock the longitudinal movement of said piston rod, and to release said locking lug from said groove to free said piston rod, and that the piston rod at its rear end is connected to a spring device for moving said piston rod forward at the administering, and a device for setting the stroke of the piston rod when the preparation is administered.

2. An injection device according to claim 1, characterized in that said locking means consist of at least two longitudinal grooves which are evenly spaced around said piston rod, and a corresponding number of locking lugs, said locking lugs having a conical shape around their outer peripheral parts with the smaller diameter at the rear and being surrounded by a tubular sleeve which rests against the outer conical parts of said locking lugs and which can be moved in the longitudinal direction such that it exerts an inward force on said locking lugs to urge them into said grooves to lock the movement of the piston rod, or release the force on said locking lugs to free the movement of said piston rod.

3. An injection device according to claim 2, characterized in that said tubular sleeve is urged against said locking lugs by means of a spring pressure in the longitudinal direction on said sleeve to urge said locking lugs into said grooves, and that said tubular sleeve by lever means may be displaced in the longitudinal direction against said spring pressure, to release the pressure on said locking lugs to free the movement of the piston rod.

4. An injection device according to claim 1, characterized in that the piston rod at its rear end is connected to a threaded coaxial sleeve which is in engagement with a threaded screw which at its rear end is provided with a stopping device which after the administering rests against the rear end of said holder device, the stroke of said piston rod being determined by the distance which said screw has been advanced into said threaded sleeve.

5. An injection device according to claim 4, characterized in that the holder device for the injection cartridge is provided at its rear end with an internal forward-facing sleeve wherein the threaded coaxial sleeve arranged at the rear end of said piston rod is slidably arranged, and that said sleeve at the rear end of said piston rod is provided with a flange which by abutting the front end of said internal forward-facing sleeve restricts the forward travel of said internal sleeve, and by this also the forward stroke of the piston rod at the administering.

6. An injection device according to claim 1, characterized in that said holder device comprises a front outer sleeve, which surrounds the injection cartridge and the locking means for the piston rod, and a rear outer sleeve, which surrounds the spring device for moving the piston rod forward at the administering and the device for determining the stroke of said piston rod, said front outer sleeve being arranged to be screwed into said rear outer sleeve such that the injection device by this movement is readied for injection by moving the rear internal forward-facing sleeve forwards against the pressure of said spring until the flange on the sleeve at the rear end of the piston rod abuts the front end of said internal forward-facing sleeve.

7. An injection device according to claim 2, characterized in that the piston rod at its rear end is connected to a threaded coaxial sleeve which is in engagement with a threaded screw which at its rear end is provided with a stopping device which after the administering rests against the rear end of said holder device, the stroke of said piston rod being determined by the distance which said screw has been advanced into said threaded sleeve.

8. An injection device according to claim 2, characterized in that said holder device comprises a front outer sleeve, which surrounds the injection cartridge and the locking means for the piston rod, and a rear outer sleeve, which surrounds the spring device for moving the piston forward at the administering and the device for determining the stroke of said piston rod, said front outer sleeve being arranged to be screwed into said rear outer sleeve such that the injection device by this movement is readied for injection by moving the rear internal forward-facing sleeve forwards against the pressure of said spring until the flange on the sleeve at the rear end of the piston rod abuts the front end of said internal forward-facing sleeve.

* * * * *